United States Patent
Perricone

(10) Patent No.: US 7,066,941 B2
(45) Date of Patent: Jun. 27, 2006

(54) APPARATUS FOR SKIN TREATMENT

(76) Inventor: Nicholas V. Perricone, 27 Coginchaug Ct., Guilford, CT (US) 06437

( * ) Notice: Subject to any disclaimer, the term of this patent is extended or adjusted under 35 U.S.C. 154(b) by 251 days.

(21) Appl. No.: 10/609,743

(22) Filed: Jun. 30, 2003

(65) Prior Publication Data

US 2004/0049247 A1   Mar. 11, 2004

Related U.S. Application Data

(63) Continuation-in-part of application No. 09/901,847, filed on Jul. 9, 2001, now abandoned.

(51) Int. Cl.
*A61N 5/06* (2006.01)

(52) U.S. Cl. .............................. 606/88; 607/89; 606/3; 606/9; 128/898

(58) Field of Classification Search .................. 606/1, 606/3, 8, 9; 607/88–91, 93; 604/289, 290; 128/898
See application file for complete search history.

(56) References Cited

U.S. PATENT DOCUMENTS

| | | | |
|---|---|---|---|
| 5,503,637 A * | 4/1996 | Kyricos et al. ............... | 607/88 |
| 5,586,981 A * | 12/1996 | Hu ................................. | 606/9 |
| 5,620,478 A * | 4/1997 | Eckhouse ...................... | 607/88 |
| 5,913,883 A * | 6/1999 | Alexander et al. ............ | 607/88 |
| 6,063,108 A * | 5/2000 | Salansky et al. .............. | 607/89 |
| 6,312,450 B1 * | 11/2001 | Yavitz et al. .................. | 607/88 |

* cited by examiner

*Primary Examiner*—A. Farah
(74) *Attorney, Agent, or Firm*—St. Onge Steward Johnson & Reens LLC

(57) ABSTRACT

Aging or damaged skin is treated by irradiating affected skin areas with an effective amount of visible light emanating from an optical apparatus and having a wavelength of about 400 nm to about 500 nm. A light source may be sunlight or artificial light, coherent or noncoherent, pulsed or continuous, of high or low energy, exposed generally or directed to target areas, or any combination of these. In one embodiment, light-emitting diodes are applied directly to discrete skin areas as needed as patches or thin sheets such as pliable masks. Green light (about 500 to about 590 nm) may be used as adjunct therapy with blue/violet light in some embodiments. Compositions containing compounds that enhance light penetration of the stratum corneum such as α-hydroxy acids (e.g., glycolic acid) and/or filter light may be applied to the skin prior to or during phototreatment.

20 Claims, 2 Drawing Sheets

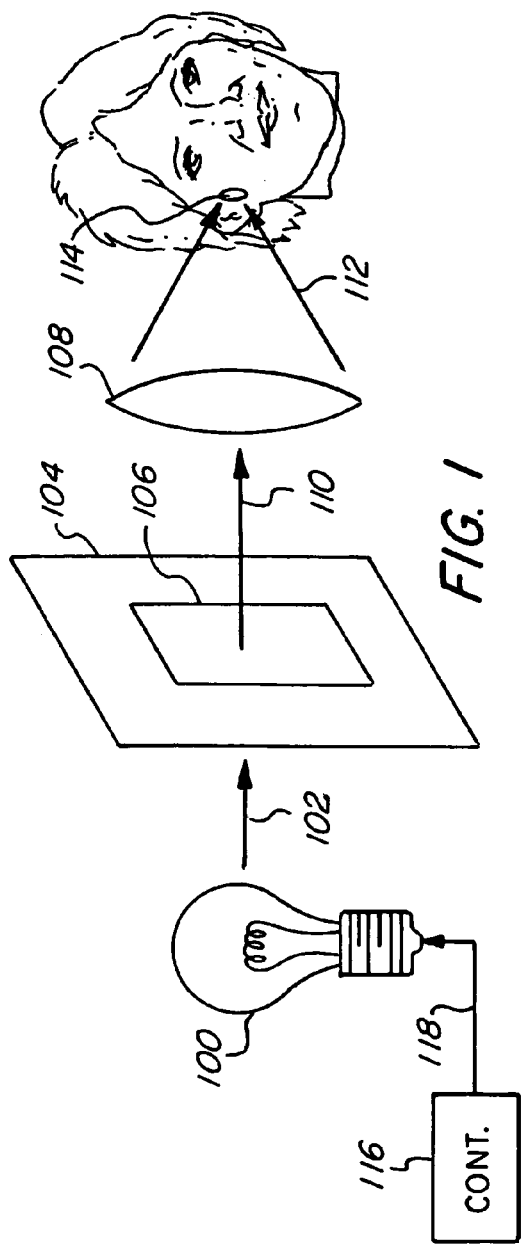
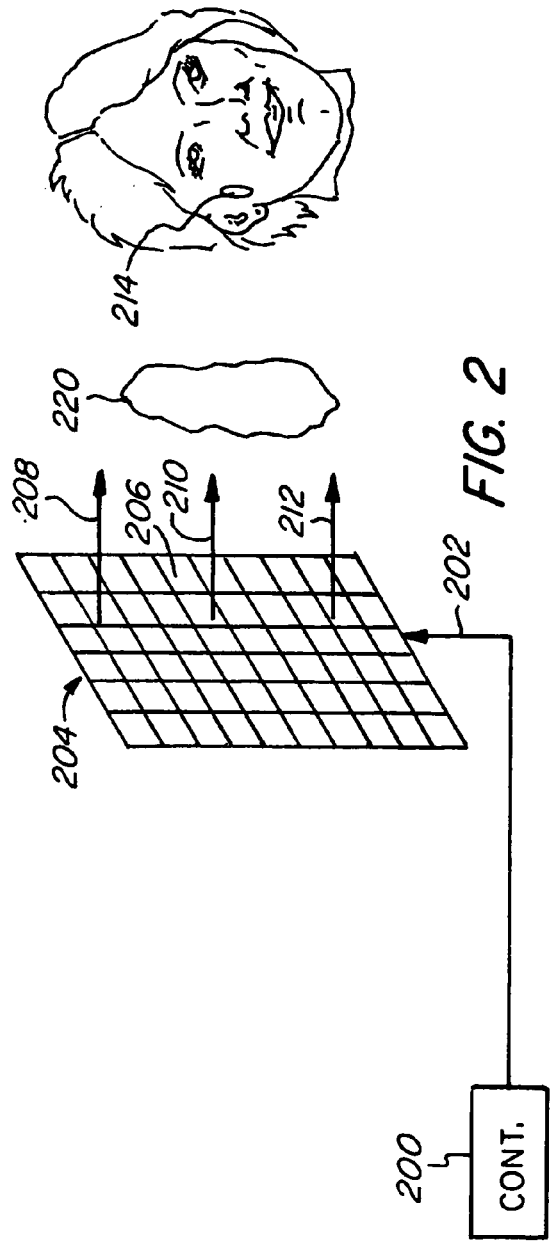

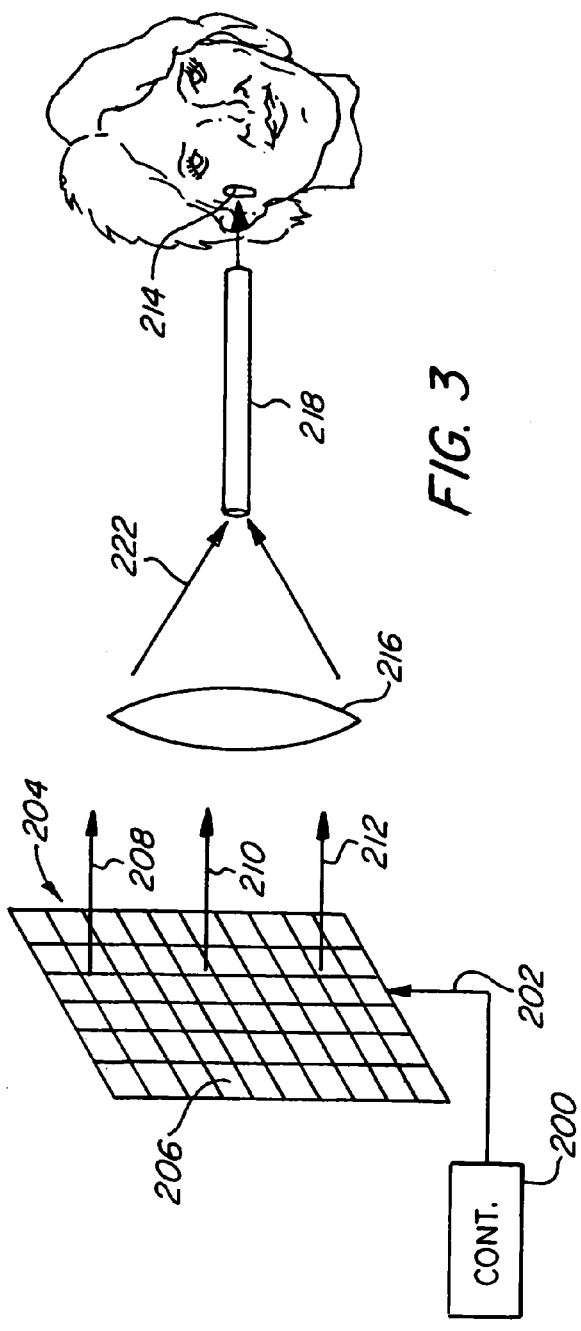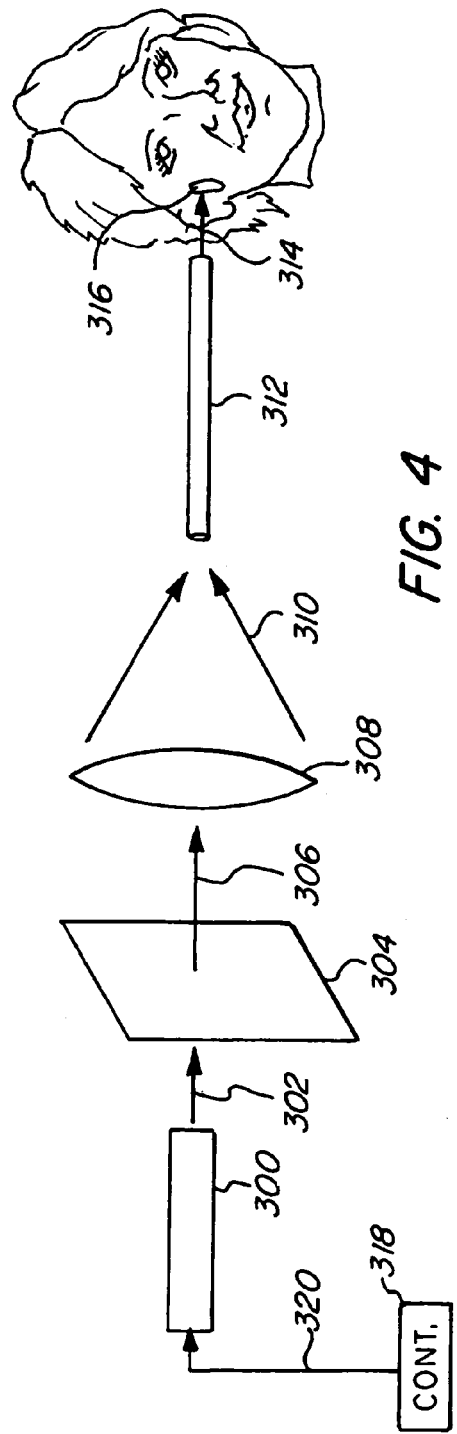

APPARATUS FOR SKIN TREATMENT

This application is a continuation in part and claims priority benefits under 35 U.S.C. §120 of U.S. patent application Ser. No. 09/901,847 filed Jul. 9, 2001 now abandoned.

FIELD OF THE INVENTION

This invention relates to an apparatus for the treatment of damaged and aging skin with light therapy, including both clinical and cosmetic phototreatments.

BACKGROUND OF THE INVENTION

Skin inflammation and aging are closely related phenomena. So similar are the processes involved with both, that aging is sometimes described dermatologically as a chronic low grade inflammatory condition. Both inflammation and aging are initiated in part by free radical damage, which takes place mostly within the cell membrane. The cell membrane is most susceptible to attack by free radicals because of its higher oxygen tension in comparison with the cotysol and its dense molecular structure largely comprising lipids and lipoproteins, which are easily oxidized by reactive oxygen species such as singlet oxygen, the superoxide anion, and hydroxyl radicals. These and other free radicals are generated in normal metabolism, as well as through ultraviolet sun exposure, exposure to other forms of ionizing and non-ionizing radiation, environmental factors such as pollution or exposure to chemicals in the home or workplace, and stresses such as infection or extreme exercise. The body's endogenous antioxidant defense systems made up of antioxidants such as vitamins C and E, glutathione, and enzymes, e.g., superoxide dismutase, are overwhelmed.

In the body's response, proinflammatory and inflammatory cascades are activated which cause the formation of toxic intermediates and end products, resulting in further, continuous, and ultimately greater damage than that caused by the initial transient reactive species. Transcription factors such as NFκB and AP1 are activated, which in turn cause production of proinflammatory mediators. These mediators, called cytokines, such as tumor necrosis factor α (TNFα) and various interleukins, cause a burst of free radicals. Arachadonic acid is released, which is itself toxic, and it is oxidized to biologically active mediators. When arachadonic acid is oxidized via the cyclooxygenase or lipoxygenase pathways, for example, prostaglandins, leukotrines, and hyroxyeicosatetraenoic acid (HETE) are produced, which cause erythma, edema, and additional free radical production accelerating the process. These and other undesirable metabolites permeate and disrupt cell membranes, mitochondrial membranes, and nuclear membranes.

Incessant membrane damage results in cross-linkage or cleavage of proteins and lipoproteins, and oxidation of membrane lipids and lipoproteins. Cell permeability is diminished, intercellular ionic concentration increases, and cellular capacity to excrete or detoxify waste products is decreased. Waste products such as lipofuscin accumulate. The increase in intercellular ionic potassium concentration causes an increase in colloid density, and m-RNA and protein synthesis are hampered, resulting in decreased cellular repair. Some cells become so dehydrated they cannot function at all. Normal metabolic phosphorylation is gradually uncoupled, resulting in cell necrosis and apoptosis. Activation of transcription factors also elicts gene expression of collagenases which cause additional damage. The ultimate result of skin aging is that the regularity of tissue structure is lost. Individual cells enlarge, but the total number of cells decreases by at least approximately 30%. Intercellular collagen increases, and the proportion of soluble collagen decreases. Cross-linking between long-chain collagen macromolecules occurs. Elastin loses its discrete structure and elasticity, and has an increased calcium content. The dermis microscars and diminishes.

Sunlight and chemical exposure wreaks far greater destruction on the skin than time itself, and intensifies and augments the aging process. There is substantial evidence that ultraviolet radiation induces the formation of reactive oxygen species that trigger the pathways producing toxic intermediates, contributing to the overall metabolic changes described above (Ibbotson, S. H., et al., *J. Investig. Derm.* 112: 933–938, 1999; this paper and others, and the patents cited herein are expressly incorporated herein in their entireties by reference thereto). Damage to the surface of the skin from sun and chemical exposure is manifested as lines, mottling, discoloration, precancers and cancers.

Early suggestions for dealing with aging and inflammatory effects on skin were predominantly aimed at lubrications and emollients through use of topical compositions containing soothing agents, e.g., commercial hand lotion products. A bewildering variety of skin creams, lotions and ointments are now available over-the-counter, which typically either act to prevent water loss from the skin or to deliver nutrients into the dermal layers. More recently, attention has been directed to agents which address the underlying processes involved in skin damage, such as the underlying free radical generation processes. In this regard, investigations have been made with respect to the antioxidants vitamin E and vitamin C to quench free radicals on the surface of the skin and to protect lipid membranes intracellularly (Wilson, R., *Drug and Cosmetic Industry,* 32–34, 38, and 68, August 1992). Dermatological compositions suggested for the treatment of damaged and aging skin that directly counteract free radical generation metabolic sequelae include tocotrienol preparations (U.S. Pat. No. 5,545,398 to Perricone), precursors of acetylcholine such as dimethylamino-ethanol (U.S. Pat. No. 5,554,647 to Perricone), fatty acid esters of ascorbic acid such as ascorbyl palmitate (U.S. Pat. No. 5,574,063 to Perricone), fructose diphosphate (U.S. Pat. No. 6,051,244 to Perricone), catecholamines (U.S. Pat. No. 5,879,690 to Perricone), and polyenylphosphatidylcholine (U.S. Pat. No. 6,191,121 to Perricone).

Damaged skin may also be removed in chemical peels. Routine medical procedures typically involve the application of particular chemicals such as trichloroacetic acid, resorcinol or salicylic acid, followed by a short reaction time to allow the chemicals to interact with damaged skin areas. Several days later, the damaged areas peel off. Peels can be uneven, however, and sometimes cause other complications such as prolonged inflammation. Less stringent methods have been developed to remedy some of these problems, such as applying tricholoracetic acid with a surfactant and an emulsifier, and then irradiating to obtain a superficial peel (U.S. Pat. No. 4,874,361 to Obagi).

Thus, it would be desirable to provide an apparatus to effect mild alternative therapies for skin damage and aging, particularly for sun damage and wrinkles, that can be used instead of, or in addition to, other methods. It would be especially desirable to provide an apparatus to effect skin treatments that continuously counteract the action of proinflammatory and inflammatory cascades involved in inflammation and aging.

SUMMARY OF THE INVENTION

It is an objective of this invention to provide an apparatus for treating aging or damaged skin by irradiation of affected skin areas with an effective amount of blue and/or violet visible light having a wavelength of about 400 nm to about 500 nm. The light may be sunlight or artificial light, coherent or noncoherent, pulsed or continuous, of high or low energy, exposed generally or directed to target areas, or any combination of these. A variety of irradiation apparatus may be employed. In one embodiment, filtered sun or artificial light is used. This can be widely exposed to skin areas, or directed to discrete skin regions, particularly to areas especially susceptible to aging, e.g., the backs of hands and the periorbital and perioral areas of the face. In an alternate embodiment, light-emitting diodes are applied directly to discrete skin areas as needed as patches or thin sheets such as pliable masks. Green light (about 500 to about 590 nm) may be used as adjunct therapy with blue/violet light in some embodiments. Compositions containing compounds that enhance light penetration of the stratum corneum such as a-hydroxy acids (e.g., glycolic acid) may be applied to the skin prior to or during phototreatment.

BRIEF DESCRIPTION OF THE DRAWINGS

FIG. 1 is a schematic diagram of a device and a filter positioned in the device and operative to pass radiation of a prescribed wavelength spectrum.

FIG. 2 is a schematic diagram of an array of light emitting diodes (LED) which may be applied directly to a skin area with or without the application of a dermatological composition.

FIG. 3 is a schematic diagram of the array of LEDs of FIG. 2 which uses an optical fiber and focusing optics to deliver radiation to a skin area.

FIG. 4 is a schematic diagram of the device and filter of FIG. 1 using a laser as a radiation source and an optical fiber and focusing optics to deliver radiation to a skin area.

DETAILED DESCRIPTION OF THE DRAWINGS

This invention is based on the surprising finding that visible short wavelength blue violet light, which is of a wavelength that typically doesn't penetrate skin well, can provide smoothness and radiance to exposed skin surfaces, resulting in a vibrant, healthy skin appearance, and can resolve erythema such as that produced by the UV effects of sunlight.

Light irradiation on skin and other tissues has been suggested for increasing the growth and proliferation of cells, including the acceleration of wound healing and skin grafts (Grossman, N., et al., *J. Invest. Dermatol.* 102:649A, 1994), the control of bacterial infection (WO 98/23329 by Lubart), and the treatment of neoplastic diseases (Colussi, V., et al., *Skin Pharm. and Appl. Skin Phys.* 11: 336–346, 1998), pigmentations (including tattoos, U.S. Pat. No. 5,217, 455 to Tan), psoriasis (U.S. Pat. No. 5,885,557 to Lentini), and acne (Sigurdsson, V., et al., *Dermatology* 194: 256–260, 1997). These typically involve either UV light (U.S. Pat. No. 3,818,914 to Bender), broad spectrum light having a wavelength between 340 and 3000 nm (ibid.), or long wavelength visible orange/red and infrared light (Lubart, R., et al., *J. Photochem. Photobiol B: Biol.* 12: 305–310, 1992 and DE 4,440,112 to Wilkens and Wilkens).

In the practice of the invention, skin is irradiated with blue/violet light having a visible wavelength of about 400 nm to about 500 nm for a time and in amounts and energy levels sufficient to provide an observable effect on the skin comprising a decrease in erythema and/or a decrease in the sensory perception of the itching/pain/irritation/warmth described by persons experiencing skin inflammation such as a sunburn, and/or the enhanced appearance of more radiant, vibrant, and healthy skin. The irradiation can be continuous or pulsed, coherent or noncoherent, of high or low intensity, or any combination of these. The light source is generated by artificial means such as lamps, lasers, or light-emitting diodes (LEDs). The blue/violet light may be applied diffusely to exposed skin areas, focused in a pattern corresponding to the configuration of affected areas, targeted to individual especially damaged areas or those particularly susceptible to aging, or delivered to specific skin regions by applying light-emitting diodes in the form of patches or sheets to discrete areas.

A preferred light source for many embodiments is sunlight. Sunlight can be filtered to provide blue violet 400 to 500 nm light using standard optical filters which then provide diffuse blue/green radiation to all of a person's exposed skin surfaces, or, by masking unaffected skin areas, delivered only to selected skin areas that are damaged or inflamed and/or have a tendency to age more than others, such as the eye and mouth regions of the face, the neck, and the backs of the hands. In the practice of this embodiment of the invention, sunlight filters that deliver blue/violet light may be incorporated into beach and picnic table umbrellas, visors, hat brims, and the like conventional devices and garments used by people in the sun. By the same token, blue/violet filters may be incorporated into the structures of sunroom roofs and the roofs of tents used for parties, camping, and eating, and into skylights, particularly the skylights of sunrooms, bathrooms, fitness centers, and indoor swimming pools where the advantages of blue/violet light exposure to skin areas outweighs the possible disadvantages of limiting the visible light spectrum delivered by the skylight to the interior. This aspect of the invention expressly includes skylights with permanent filters that provide exclusively blue/violet light and those that have removable filters that can be controlled to provide blue/violet light at some times, and other light, including full spectrum visible light, at others, such as conventional skylights having blue/violet light shutters. Once installed, the filtered light effortlessly provides continuous benefits to the skin.

Other embodiments employ artificial light such as filtered sunlamp and halogen lamps, flash lamps, filtered fluorescent light, including converted red light (e.g., that disclosed in JP 9054562 to Mitsubishi), light arrays (e.g., U.S. Pat. No. 3,818,914, cited above), and light arranged in a pattern corresponding to affected skin areas (e.g., U.S. Pat. No. 5,944,748 to Mager, et al.). These can be modified to provide special light distribution devices such as that described by Mori, in U.S. Pat. No. 4,838,271. Also encompassed by the invention are indoor lights equipped with permanent or removable filters; like sunlight filters, artificial light filters may be of particular benefit in bathrooms, fitness centers, indoor swimming pools, etc., and used on fixtures that provide either continuous or occasional blue/violet light, depending upon the light design.

As summarized above, LEDs are employed as patches, sheets and the like in alternate embodiments, as these provide an energy source and focused energy delivery to discrete skin areas. Preferred among these are thin, flexible, pliable sheets having embedded LEDS which can be applied to specific regions of the body and are easy to use. One particularly preferred embodiment is an LED face mask, which may have a neck collar as an auxiliary component. An advantage of LED patches or sheets is that they can be easily coupled to optical fibers that simplify light delivery to the treatment region, and the wavelength, pulse length, exposure times, and energy density can be well controlled.

Lasers are used in alternate embodiments, and are a practical light source for some treatments because their high power output at the appropriate wavelength can minimize exposure times. Like LEDs, laser light can be easily coupled to optical fibers that simplify light delivery to the treatment region, and the wavelength, pulse length, exposure times, and energy density can be well controlled. Lasers include, but are not limited to, tunable dye or solid-state lasers, metal vapor lasers, and diode lasers.

Light intensity may be varied from high to low, or mixtures thereof. By "low intensity" is generally meant light having an intensity of below about 800 mW/cm$^2$. By "high intensity" is generally meant light having an intensity of above about 800 mW/cm$^2$. A watt is one Joule per second, and optimal irradiation can be gradually and incrementally increased or decreased by 1 to 20 Joules at will or as needed as set out by Tan in U.S. Pat. No. 5,217,455 to achieve optimal results.

Encompassed by the invention is an apparatus for phototreatments that employ green light as adjunct therapy during or after treatment with blue/violet light. By "green" light is meant visible light having a wavelength of about 500 to about 590 nm. Green light may be used together with blue/violet light in some embodiments, either continuously, intermittently, or alternately. In other embodiments, an apparatus for green light therapy is used after the blue/violet light treatment. In embodiments where green light is used, it is delivered by any of the means described above for the delivery of blue/violet light. It is an advantage of this embodiment that green light can be added to phototreatment of the invention simply by slightly enlarging the visible spectrum of the light shone on the skin. It is another advantage of this embodiment that some positive effects reported for green light therapy may be obtained, such as stimulated cellular repair and removal of fine lines and wrinkles, may enhance results obtained using the phototreatment of the invention.

Dermatological compositions containing chemical or physical filters may be administered to skin prior to light therapy in embodiments that employ blue light alone and those that employ blue light and green light. By a "composition containing a chemical filter" is meant compositions containing one or more compounds that screen out light having a wavelength below about 400 nm and above about 500 nm for the embodiment using blue light alone, and one or more compounds that screen out light having a wavelength below about 400 nm and above about 590 nm for the embodiment employing blue and green light, in a dermatologically acceptable carrier. By a "composition containing a physical filter" is meant a composition containing fine glass beads, liposomes containing particulate substances that defract light of certain wavelengths, and the like, in a dermatologically acceptable carrier. In the typical practice of this embodiment of the invention, a cream or lotion composition containing at least one chemical filter and/or at least one physical filter are applied to the skin prior to light therapy according to the invention. It is an advantage of this embodiment that any unfiltered light source may be employed.

One or more active compounds or compositions that enhance light therapy according to the invention, including the chemical and optical transparency of the stratum corneum and, most preferably skin absorption of radiation in the blue violet spectral region between about 400 and about 500 nm, are applied in dermatological compositions prior to or during phototreatments of the invention in some embodiments. As used herein, these agents are collectively called "photopenetration enhancers", and specifically include agents that block visible radiation at wavelengths above the blue/violet region of about 400 to about 500 nm region. Photopenetration enhancers include, but are not limited to, α-hydroxy acids. As used herein, the term "α-hydroxy acid" has reference to and encompasses the general class of organic compounds containing at least one hydroxy group and at least one carboxyl group, and wherein at least one hydroxyl group is located on the α-carbon atom. Typically, the compounds are organic acids having at least one carboxylic acid group and at least one hydroxyl group on the α-carbon atom, and may contain other functional groups including additional hydroxyl and carboxylic acid moieties. Preferred α-hydroxy acids and/or α-hydroxy acid derivatives are less bulky structurally so that they penetrate the skin well, and thus have a backbone of from one to three carbon atoms such as those set out in U.S. Pat. No. 5,965,618 at column 6 lines 4 to 29. Where employed, glycolic and/or lactic acid or their derivatives are preferred; glycolic acid is especially efficacious.

Where photopenetration enhancers are employed, topical administration to exposed skin sites prior to irradiation is preferred. Only effective amounts are needed to enhance light therapy, and so generally enhancement is achieved by applying the agents to exposed or affected skin sites. This is typically accomplished in association with a carrier, and particularly one in which the agent is soluble per se or is effectively solubilized (e.g., as an emulsion or microemulsion). Where employed, the carrier is inert in the sense of not bringing about any adverse effect on the skin areas to which it is applied. Suitable carriers include water, alcohols, oils and the like, chosen for their ability to dissolve or disperse the agents and any other ingredients used in the treatment. Generally, even low concentrations in a carrier are suitable, depending upon the application regimen and adjunct ingredients employed. Many embodiments contain from about 1% to about 15% by weight, more narrowly from about 5% to about 10% by weight photopenetration enhancers. Where glycolic acid is employed as a photopenetration enhancer, typcal concentrations range from about 1% to about 10% by weight, more narrowly from about 3% to about 7%, by weight glycolic acid.

Compositions containing fat-soluble fatty acid esters of ascorbic acid (vitamin C) may be applied to the skin before, during, or after blue/violet light treatments of the invention. Alternatively, fat-soluble fatty acid esters of ascorbic acid may be added as an adjunct ingredient to compositions containing photopenetration enhancers. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof.

In FIG. 1, an apparatus for treating aging or damaged skin is shown. The apparatus comprises a 104 such as an umbrella, a visor or a hat brim. An optical filter 106 is positioned within or on the 104 and is operative to allow to pass radiation 102 emanating from a source 100 having a wavelength of about 400 nm to about 500 nm. The filtered radiation 110 may be focused by focusing optics 108 to a skin area 114 suffering from the effects of aging or damage. The radiation source 100 is controlled by a control signal 118 emanating from a controller 116. The controller 116 thus can cause to produce continuous wave or pulsed radiation. As seen in FIG. 4, the radiation source 100 of FIG. 1 may comprise a laser 300 also controlled at 318, 320 to produce continuous wave or pulsed radiation 302. As further seen in FIG. 4, the filter 304 need not be placed in one of the aforementioned devices 104. In FIG. 4, filtered radiation 306 is focused at 308, 310 to a waveguide such as an optical fiber 312 for delivery to a skin area 316.

In FIG. 2, an array of light sources such as an array of LEDs 204 is shown. Each LED 206 is controlled by a control signal 202 emanating from a controller 200 so as to cause to produce continuous wave or pulsed radiation 208, 210, 212. The radiation may comprise radiation having a wavelength of about 400 nm to about 500 nm or about 500 nm to about 590 nm or a combination thereof 212. A dermatological composition 220 may also be applied to the skin area 214 as the radiation 208, 210, 212 is applied to the skin area 214.

In FIG. 3, the radiation 208, 210, 212 from the array of LEDs 204 may be focused at 216 to a waveguide such as an optical fiber 218 for delivery to a skin area 214 with or without a dermatological compound 220.

Preferred apparatus and methods of the invention are easy to use and non-invasive. A particular advantage of some embodiments is simplicity. Exposed skin surfaces may be treated for damage and aging by merely sunbathing, gardening, or picnicking outdoors under a blue/violet light filter in an umbrella, hat brim or visor, or in a room with a blue/violet filtered skylight or artificial light. LED masks provide phototherapeutic facials. A further advantage of the invention is that its methods can involve the use of no chemicals applied to hyperallergenic or normal skin.

The efficacy of the light treatment methods of the invention was illustrated in observations involving the exposure of the skin of patients having a sun or chemical burn presenting with a low grade, visibly perceptible erythema. The slightly inflamed skin areas were half masked, and exposed to blue/violet filtered summer sunlight or sunlamp light for two hours. Inflammation in skin regions exposed to blue/violet filtered light resolved in approximately half the time as non-treated skin regions in all individuals. Moreover, most patients reported that phototreated skin areas felt less itchy, irritated, painful, and warm. Individuals with normal skin reported that a two-hour sunbath in blue/violet light made their skin observably smoother, more radiant, vibrant and healthy-looking.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A system for treating aging or damaged skin, the system comprising:
    a sheet comprising an array of light emitting diodes for direct application to the skin wherein a portion of the array of diodes generate radiation having a wavelength of about 400 nm to about 500 nm; and
    a dermatological composition for application to the skin the dermatological composition containing a physical filter for filtering the radiation emanating from the array of light emitting diodes the physical filter comprising fine glass beads or liposomes containing particulate substances for diffracting light at prescribed wavelengths.

2. The system as set forth in claim 1 wherein the dermatological composition further consists of a chemical filter.

3. The system as set forth in claim 1 wherein another portion of the array of light emitting diodes generate radiation having a wavelength of about 500 nm to about 590 nm.

4. The system as set forth in claim 1 wherein the radiation has an intensity of below about 800 mW/cm$_2$.

5. The system as set forth in claim 1 wherein the radiation has an intensity of above about 800 mW/cm$^2$.

6. The system as set forth in claim 1 wherein the radiation is continuously illuminated on the skin.

7. The system as set forth in claim 1 wherein the radiation is pulsed.

8. The system as set forth in claim 1 further comprising a dermatological composition that enhances the optical transparency of the stratum corneum.

9. The system as set forth in claim 8 wherein the composition comprises an alpha-hydroxy acid.

10. The system as set forth in claim 9 wherein the alpha-hydroxy acid is glycolic acid.

11. A method for treating aging or damaged skin, the method comprising the steps of:
    providing an array of light emitting diodes wherein a portion of the array of diodes generate radiation having a wavelength of 400 nm to about 500 nm;
    providing a dermatological composition for application to the skin the dermatological composition containing a physical filter the physical filter comprising fine glass beads or liposomes containing particulate substances for diffracting light at prescribed wavelengths;
    applying said dermatological composition to aging or damaged skin;
    applying said array of light emitting diodes directly to aging or damaged skin; and
    transmitting radiation from said array of light emitting diodes to aging or damaged skin.

12. The method as set forth in claim 11 wherein said dermatological composition application further consists of a chemical filter.

13. The method as set forth in claim 11 wherein another portion of said light emitting diodes generate radiation having a wavelength of about 500 nm to about 590 nm.

14. The method as set forth in claim 11 wherein the said transmitted radiation has an intensity of below about 800 mW/cm$^2$.

15. The method as set forth in claim 11 wherein the said transmitted radiation has an intensity of above about 800 mW/cm$^2$.

16. The method as set forth in claim 11 wherein the said transmitted radiation is continuously illuminated on the skin.

17. The method as set forth in claim 11 wherein the said transmitted radiation is pulsed.

18. The method as set forth in claim 11 further:
providing a dermatological composition that enhances the optical transparency of the stratum corneum; and
applying said dermatological composition to aging or damaged skin.

19. The method as set forth in claim 18 wherein the said composition further comprises an alpha-hydroxy acid.

20. The method as set forth in claim 19 wherein the said alpha-hydroxy acid is glycolic acid.

* * * * *